United States Patent [19]

Fedor

[11] Patent Number: 5,592,286
[45] Date of Patent: Jan. 7, 1997

[54] CONTAINER FLANGE INSPECTION SYSTEM USING AN ANNULAR LENS

[75] Inventor: Richard L. Fedor, Mantua, Ohio

[73] Assignee: Alltrista Corporation, Muncie, Ind.

[21] Appl. No.: 400,359

[22] Filed: Mar. 8, 1995

[51] Int. Cl.⁶ .............................. G01N 21/00; H04N 7/18; H04N 9/47
[52] U.S. Cl. ...................... 356/240; 359/711; 250/223 B; 382/142; 348/127
[58] Field of Search .................................. 356/237, 240, 356/428; 348/91–92, 125–128; 382/141–143; 250/223 B; 359/662, 668, 708, 711, 718, 721

[56] References Cited

U.S. PATENT DOCUMENTS

| | | | |
|---|---|---|---|
| 2,466,161 | 4/1949 | Doll | 88/24 |
| 2,798,605 | 7/1957 | Richards . | |
| 3,107,011 | 10/1963 | Mathias et al. . | |
| 3,171,033 | 2/1965 | Mathias et al. | 250/224 |
| 3,711,722 | 1/1973 | Kavanagh | 359/711 |
| 3,857,637 | 12/1974 | Obenreder | 356/237 |
| 3,886,356 | 5/1975 | Gomm et al. | 250/223 B |
| 3,894,806 | 7/1975 | Remy et al. | 356/240 |
| 4,026,656 | 5/1977 | Kusz et al. | 356/240 |
| 4,280,624 | 7/1981 | Ford | 209/524 |
| 4,284,353 | 8/1981 | Yoshida et al. | 356/240 |
| 4,330,205 | 5/1982 | Murakami et al. | 356/237 |
| 4,376,951 | 3/1983 | Miyazawa | 356/237 |
| 4,378,159 | 3/1983 | Galbraith | 356/237 |
| 4,391,373 | 7/1983 | Wiggins | 209/526 |
| 4,424,441 | 1/1984 | Bieringer et al. | 250/223 B |
| 4,428,674 | 1/1984 | Giebel et al. | 356/240 |
| 4,435,641 | 3/1984 | Hajime | 250/223 B |
| 4,459,023 | 7/1984 | Reich et al. | 356/237 |
| 4,506,980 | 3/1985 | Pryor et al. | 356/237 |
| 4,511,222 | 4/1985 | Biren . | |
| 4,538,909 | 9/1985 | Bible et al. | 356/237 |
| 4,560,273 | 12/1985 | Ando et al. | 356/237 |
| 4,583,854 | 4/1986 | Lozar | 356/237 |
| 4,606,635 | 8/1986 | Miyazawa et al. | 356/240 |
| 4,626,079 | 12/1986 | Nakamura et al. . | |
| 4,650,326 | 3/1987 | Nagamine et al. | 356/240 |
| 4,682,023 | 7/1987 | Yoshida | 250/223 B |
| 4,691,231 | 9/1987 | Fitzmorris et al. | 356/240 |
| 4,758,084 | 7/1988 | Tokumi et al. | 356/237 |
| 4,760,270 | 7/1988 | Miller | 250/263 |
| 4,865,447 | 9/1989 | Shay | 356/240 |
| 4,871,257 | 10/1989 | Suzuki et al. | 356/400 |
| 4,912,318 | 3/1990 | Kajiura et al. | 250/223 B |
| 4,914,289 | 4/1990 | Nguyen et al. | 250/223 B |
| 4,924,107 | 5/1990 | Tucker | 356/241 |
| 4,965,454 | 10/1990 | Yamanchi et al. | 356/237 |
| 5,030,823 | 7/1991 | Obdeijn | 250/223 B |
| 5,072,127 | 12/1991 | Cochran et al. | 250/223 B |
| 5,142,416 | 8/1992 | Nakamura et al. | 359/711 |
| 5,216,481 | 6/1993 | Minato | 356/240 |
| 5,220,400 | 6/1993 | Anderson et al. | 356/241 |
| 5,249,034 | 9/1993 | Minato | 356/375 |

*Primary Examiner*—Vincent P. McGraw
*Assistant Examiner*—Jason D. Eisenberg
*Attorney, Agent, or Firm*—Brinks Hofer Gilson & Lione

[57] ABSTRACT

The present invention provides a machine vision inspection system for inspecting the flanges of metal containers that can reliably detect flange defects as small as 0.010 to 0.012 inches. The inspection device comprises apparatus for producing an enlarged image of selected portions of the flange and apparatus for capturing and processing the image. The apparatus for producing the enlarged image includes an annular lens positioned between the flange and the producing apparatus. The invention also provides a method for inspecting a flange of an article, such as a can, for defects. The method comprises the steps of directing light onto the flange of the article from a light source, forming light rays reflected from the flange into a radially expanded image of the flange by positioning an annular lens to redirect reflected light rays into the radially expanded image, and providing apparatus for capturing and processing the image to inspect the flange for defects. By providing an annular lens positioned between the flange and the camera, the present invention enlarges the image of the flange and any defects relative to a pixel of an inspection system. Increasing the effective size of a defect to extend outside of a single pixel increases the effective resolution of the system permitting the detection of smaller defects in the flange of a metal container.

27 Claims, 5 Drawing Sheets

CONTAINER FLANGE INSPECTION SYSTEM USING AN ANNULAR LENS

FIELD OF THE INVENTION

The present invention relates to article inspection systems and particularly to systems for inspecting beverage cans and the like. More particularly, the invention relates to systems for inspecting the flanges formed around the open mouth of cans and the like for defects.

BACKGROUND OF THE INVENTION

During the manufacturing of metal food containers, a number of defects in the flange may exist which should cause the can to be rejected, such as nicks, dents, knockdowns and the like, as well as grease, oil, blistered or nonuniform coatings, and debris. Such flaws or defects are sometimes produced during the manufacturing process and/or as a result of contamination after manufacture, but prior to the filling of the container. Small defects in the flange of a metal container can be especially troublesome. Such defects can be too small to be detected by conventional machine inspection techniques, yet still be large enough to interfere with the proper sealing of the can, thereby permitting leakage or contamination of the contents.

Machine vision is the technology of acquiring or sensing an image of a selected portion of the container through an electronic sensor and determining the existence of any marks or defects in the image and the acceptability of any such marks or defects by use of a vision computer. In typical machine vision technology, a television camera acquires an image and a dedicated vision computer processes and analyzes the image.

While human vision may outperform its automatic equivalent in its sheer ability to analyze very complex, everyday scenes, when it comes to repeated tasks, such as the inspection of aluminum beverage containers over and over again, a human observer understandably tires, loses concentration, and makes mistakes. Machine vision inspection of metal containers is known to provide some important advantages, including sophisticated image processing/analysis, repeatable performance, image acquisition for diagnosis and setup, ability to inspect a variety of containers, and large tolerance in required part placement. Moreover, at conveyor line speeds of up to 2000 containers per minute, each container spends about 30 milliseconds at an inspection station. At those speeds, only a machine vision system is fast enough to reliably, and repeatably, inspect a container in that amount of time.

Machine inspection of glassware is well known. See, for example, U.S. Pat. No. 4,758,084 to Tokumi, et al., U.S. Pat. No. 4,914,289 to Nguyen, et al., and U.S. Pat. No. 4,682,023 to Yoshita. However, machine inspection of metal containers presents unique problems.

First, the containers are inherently opaque, so the inspection system must operate on the light reflected from the metallic surfaces of the selected areas being inspected, as compared to glassware inspection systems which sense or capture light passing through the glassware. Second, some small defects in the flange may be too small to be detected by conventional machine vision techniques, yet because of the way that the container top is attached to the flange, some of those small defects may still be large enough to prevent proper sealing. For example, conventional machine vision techniques can reliably detect defects having a size on the order of 0.040 inch. However, the salmon industry requires detection of 0.014 to 0.020 inch defects. Thus, a need exists for a reliable and economical method of detecting small defects in the flange of a metal container that might otherwise interfere with the proper sealing of the container.

SUMMARY OF THE INVENTION

The present invention provides a machine vision inspection system for inspecting the flanges of metal containers that can reliably detect flange defects as small as 0.010 to 0.012 inches.

Machine vision systems rely on television or video cameras to image the article to be inspected and detect any flaws. The image produced by the camera is a collection of individual picture elements (pixels). The camera's resolution, or ability to detect a flaw, is directly related to the camera's pixel size. Therefore, once a camera is selected for use with a conventional machine vision inspection system, the resolution of that system is determined, and any flaw that is smaller than a single pixel will go undetected. Of course, the resolution of the system can be improved in order to reduce the size of the minimum detectable flaw, but that involves more expensive and, possibly, more complex equipment. Thus, it is preferable to seek other ways to improve the effective resolution of the camera.

According to the present invention, an inspection device for inspecting the flange of a container comprises means for producing an enlarged image of selected portions of the flange and means for capturing and processing the image. The means for producing the enlarged image includes an annular lens positioned between the flange and the producing means.

The annular lens can take on different shapes according to the particular application. For example, in one embodiment, the annular lens is generally toroidal and is adapted to produce an enlarged image of the peripheral edge of the flange. In another embodiment, the annular lens includes a first planar surface, a central axis orthogonal to the planar surface, and a second surface. The second surface extends away from the first surface so as to provide a maximum lens thickness at some predetermined radial distance from the central axis.

The invention also provides a method for inspecting a flange of an article, such as a can, for defects. The method comprises the steps of directing light onto the flange of the article from a light source, forming light rays reflected from the flange into a radially expanded image of the flange by positioning an annular lens to redirect reflected light rays into the radially expanded image, and providing means for capturing and processing the image to inspect the flange for defects. The annular lens includes a central axis and the lens is configured to include a maximum lens thickness at a first radial distance from the central axis and a minimum lens thickness at a second radial distance from the central axis.

In both the apparatus and method of the invention, the capturing and processing means includes a video camera having a lens and a vision computer. According to one aspect of the invention, the video camera lens is movable along the central axis relative to the annular lens so as to expand the image to be captured.

By providing an annular lens positioned between the flange and the camera, the present invention enlarges the image of the flange and any defects relative to a pixel of an inspection system. Increasing the effective size of a defect to extend outside of a single pixel increases the effective resolution of the system permitting the detection of smaller defects in the flange of a metal container.

Additional objects, features, and advantages of the invention will become apparent to those skilled in the art upon consideration of the following detailed description of a preferred embodiment exemplifying the best mode of carrying out the invention as presently perceived.

DETAILED DESCRIPTION OF THE DRAWINGS

Figure 1:
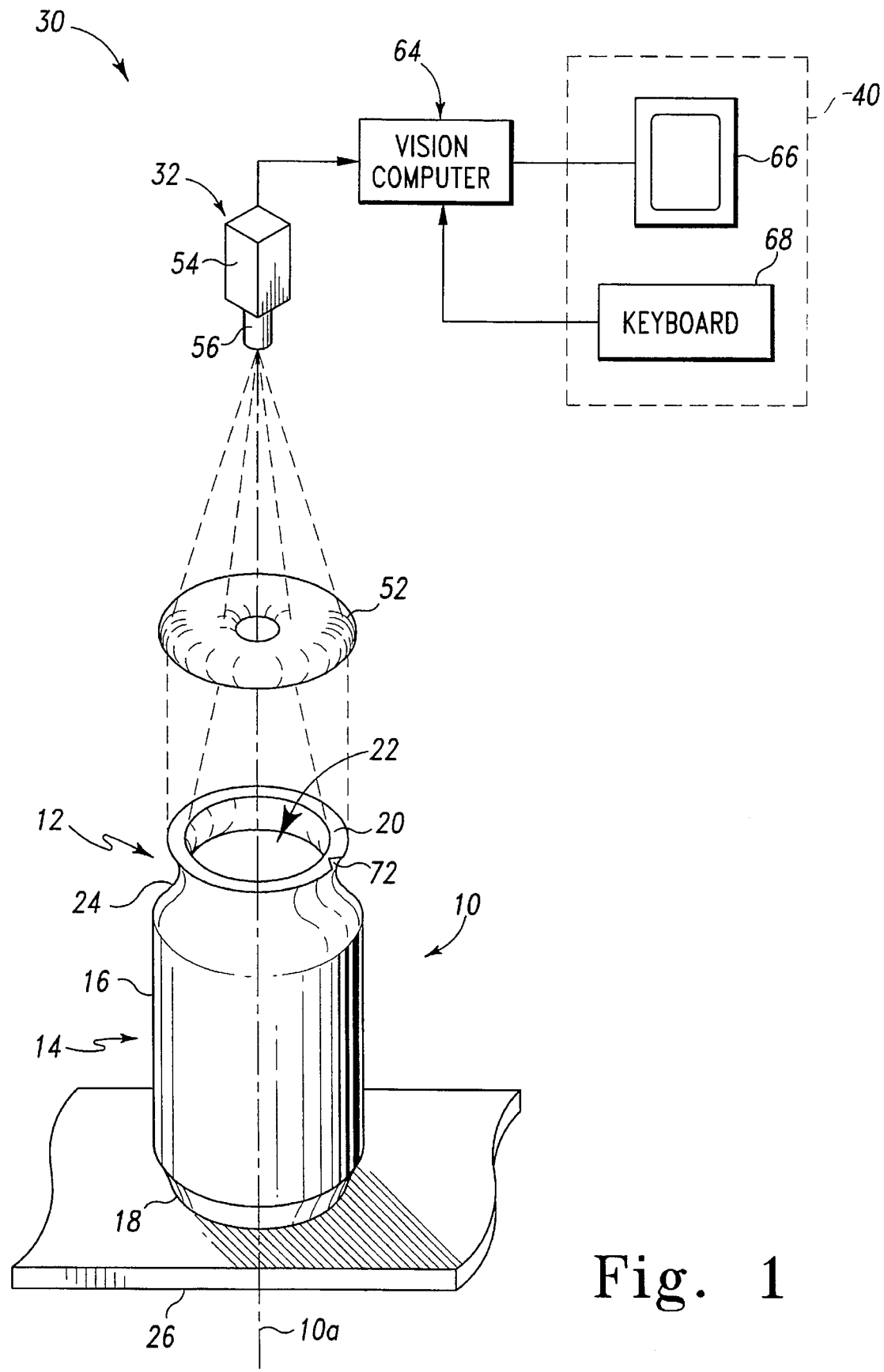
FIG. 1 is a perspective view of a lens according to the present invention positioned between the vision inspection system and the flange of a container to be inspected.

This invention generally presents a system and method for inspecting the flange of an opaque object, such as a typically formed metal beverage container 10 as shown in FIG. 1. Such a metal beverage container 10 commonly includes an upper portion 12 and a lower portion 14 defined by a cylindrical sidewall 16 and a bottom wall 18. Upper portion 12 includes a top surface defined by flange 20 circumscribing the open top 22 of the container 10 and a neck portion 24 of reduced diameter relative to the cylindrical sidewall 16 of the container 10. For quality control considerations, the flange 20 must be round and free of nicks, dents, knockdowns and the like.

This invention is preferably used with a system 30 located at an inspection station 26, including means 28 (FIG. 2) for illuminating the flange 20 of container 10, image-capturing means 32 located above the container 10 for capturing an image of the flange 20, and, preferably, an image-processing means 34 coupled to the image-capturing means 32 for electronically analyzing the image for defects.

System 30 used with this invention can further include operator interface means 40 coupled to system 30 for allowing an operator to communicate with the system 30. Even further, system 30 can include machine interface means (not shown) for allowing the system 30 to communicate with remote machines, such as a rejection machine 94 (FIG. 3), to effect the removal of defective containers from the conveyor line.

Figure 2:
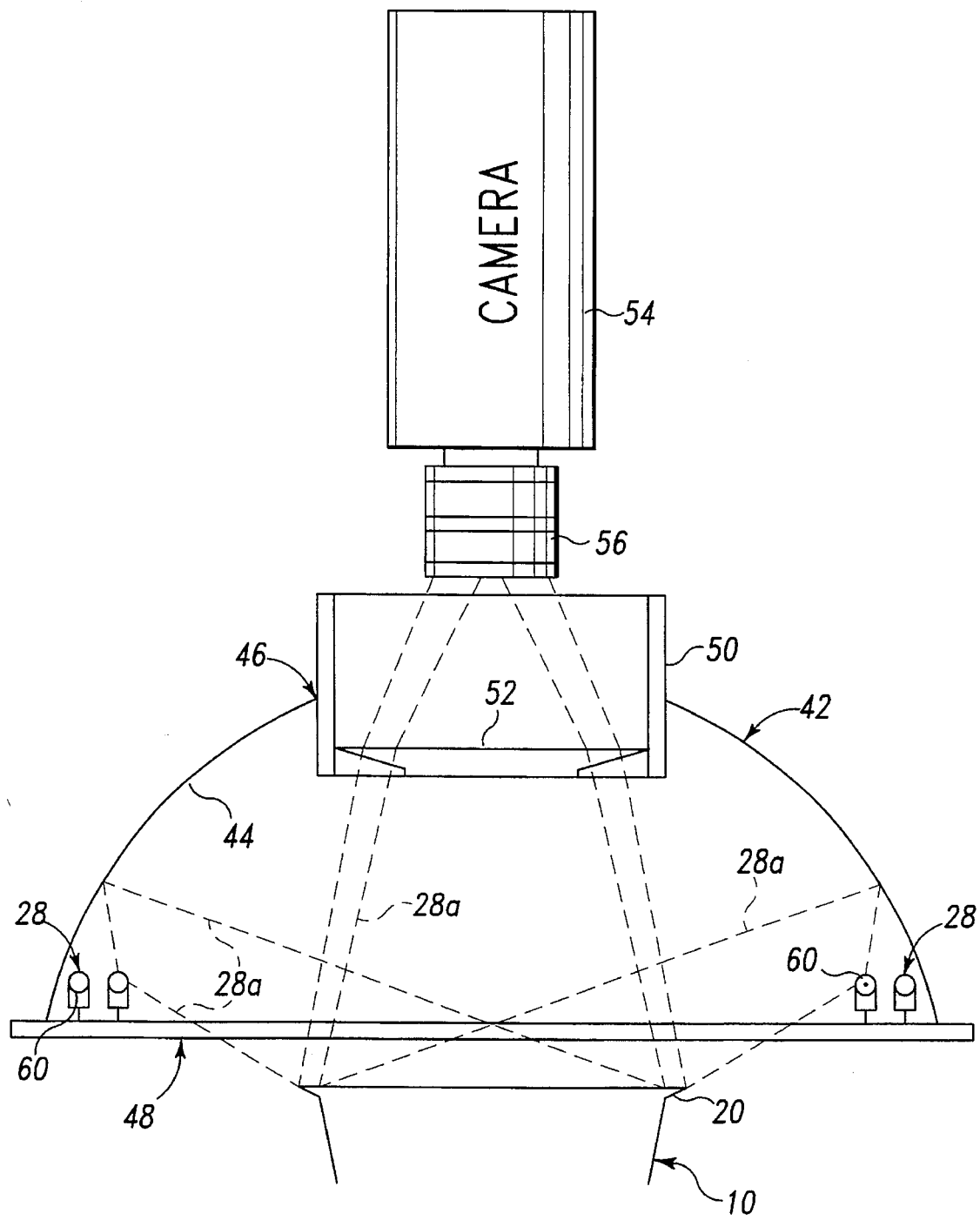
FIG. 2 shows an annular lens positioned inside a diffuser bowl to form an enlarged image of the flange of a can at a camera.

As shown in FIG. 2, image-capturing means 32 preferably comprises an annular diffuser bowl 42 having an inwardly facing surface 44, an upper opening 46 and a lower opening 48. A tube 50 is positioned in the upper opening 46 and coaxially aligned with the image-capturing means 32 and the container 10. To provide for the effective enlargement of the image of the flange 20, annular lens 52 is positioned in the tube 50.

The image-capturing means 32 employed by system 30 preferably comprises a television camera 54 equipped with a lens 56. Lens 56 of camera 54 is specifically provided with the proper aperture and depth of focus to encompass and capture the enlarged image of the flange 20 of container 10 formed by the annular lens 56.

Illuminating means 28 used with this invention preferably comprises an annular array 60 of light-emitting diodes disposed in the diffuser bowl 42 in a front-lighting arrangement in relation to container 10. Annular array 60 is preferably located above the open top of container 10 and below the lens 56 and is adapted to direct light rays 28a generally downwardly and radially inwardly to illuminate particularly the flange 20. Such an arrangement causes light rays 28a to illuminate the flange 20 generally, and the peripheral edge in particular.

Camera 54, annular diode array 60, tube 50 and annular lens 56 are preferably arranged generally coaxially, that is, so that their central axes generally coincide with each other, and with central axis 10a of container 10.

Figure 3:
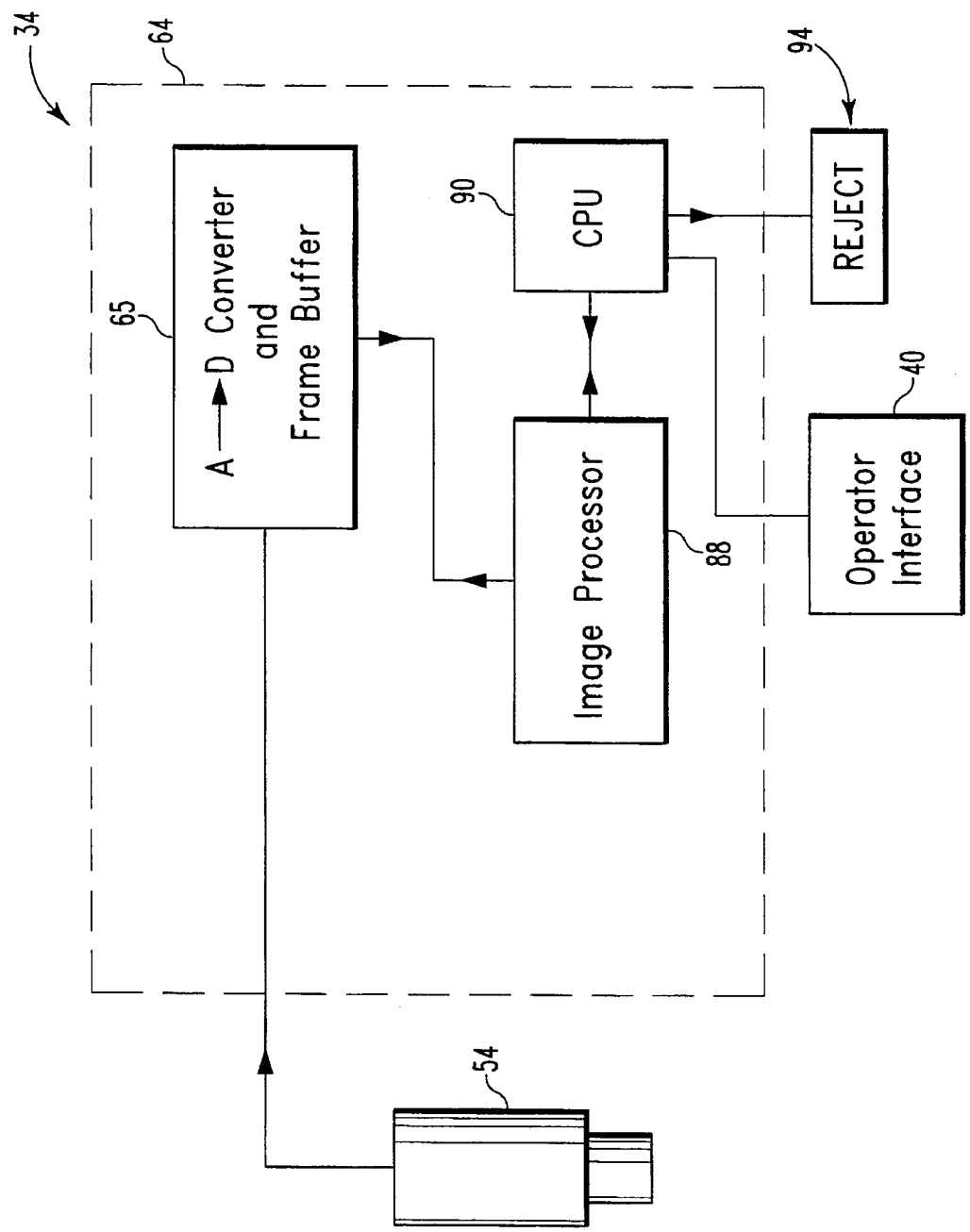
FIG. 3 is a block diagram of a representative machine vision inspection system.

As shown in FIGS. 1 and 3, image processing means 34, defined by a vision computer 64 and operator interface means 40, are preferably coupled to camera 54 to receive the flange image and to provide for the programming of system 30 by the use of a monitor 66, menus presented thereon, and a keyboard 68.

Because material handling systems are seldom able to position the container to be inspected precisely in the desired location, there is frequently a slight deviation between the central axis 10a of the container and the central and optical axis of the inspection system. Lens 56 must therefore have sufficient field of view to accommodate resulting deviating light rays from flange 20. Preferably, part-present sensors (not shown) are employed to strobe illuminator 60 and initiate the inspection sequence when the container is positioned very near the center of system, as is well known in the art.

The camera 54 used with this invention is adapted to capture and store images for a brief moment (milliseconds) in a memory matrix array, which comprises a plurality of separate memory locations, each of which represents a single pixel. Camera 54 thus converts the expanded image of the flange into information corresponding to each of the plurality of pixels. For each pixel the camera 54 generates a signal corresponding to a very small area of the flange. The camera 54 acts as a source of image signals that can be directed to the vision computer 64 used with this invention. The vision computer can be operated to identify unacceptable marks (such as defect 76 in FIG. 4) and cause the removal of an unacceptable container from the conveyor line.

The camera 54 employed by this invention preferably comprises a high sensitivity, high resolution, solid state, MOS (metal oxide semiconductor) television camera with a sensitivity of at least 5 Lux. Such a camera is capable of capturing the images of the flange of the container, all while the container is moving along a conveyor line. A camera suitable for use with this invention is available from Panasonic Corporation, Model GP-MF 702/Industrial MOS B/W camera, equipped with a 50 mm lens.

The vision computer 64 utilized with this invention is preferably based upon a multi-processor system design comprising an analog-to-digital converter and frame buffer means 65, an image processor 88, and a CPU 90. A–D converter and frame buffer means 65 is adapted to digitize the image signals received from the camera 54 for each pixel, and then store the resultant digitized information for the image of the flange. After the digitized image has been stored in frame buffer 86, the digitalized image information is then ready to be analyzed by the image processor 88. The instructions for these processing operations may be provided by a PROM or CPU 90 or may be communicated through the operator interface 40. In general, the image processor 88 and CPU analyze the digitized image information to identify pixel information corresponding to unacceptable defects by comparison with criteria of unacceptability provided by an operator through interface 40. Image processor 88 executes these instructions using predetermined stored parameters retrieved from a CPU RAM. The results of the inspection job may then be directed into a mailbox memory means for subsequent use by the CPU 90.

A suitable vision computer 64 for use with this invention may be provided by the processing unit commercially available from LumenX, a division of Alltrista Corporation, Mogadore, Ohio, as a product trademarked as FAST TRACK. The FAST TRACK machine vision processing unit converts the image sensed by the camera 54 into binary images by applying an edge detection algorithm. An example of the operation of the FAST TRACK unit is discussed in detail in U.S. Pat. No. 4,924,107, the disclosure of which is hereby incorporated by reference.

As noted above and as shown in FIGS. 1 and 3, user interface 40 allows an operator to communicate with the system 30 of this invention and generally includes the monitor 66, keyboard 68 and can include an LED remote I/O display (not shown). The monitor 66 displays the video image of the flange 20 of the container 10 being inspected, as well as various prompts and instructions directed to the operator. The system can additionally include machine interface means for allowing the system to communicate with remote rejection machines 94. Such rejection machines 94 can be provided by various conventional pneumatically actuated rejection devices.

This invention may be integrated into a container manufacturing line to allow 100 percent inspection of containers. In such an operation, additional apparatus may be employed in combination with this invention. Such additional apparatus may include part-present detectors to detect the presence of a container at the inspection stations and deliver an appropriate signal to initiate the inspection sequences, and/or to detect the presence of a container at the rejection station and deliver an appropriate signal to initiate a rejection sequence. Should the invention detect an unacceptable defect or flaw as determined by the vision computer 64, the system 30 may generate an appropriate rejection signal directed to a remote rejection machine 94 to initiate the removal of the unacceptable container from the manufacturing line.

Figure 4:
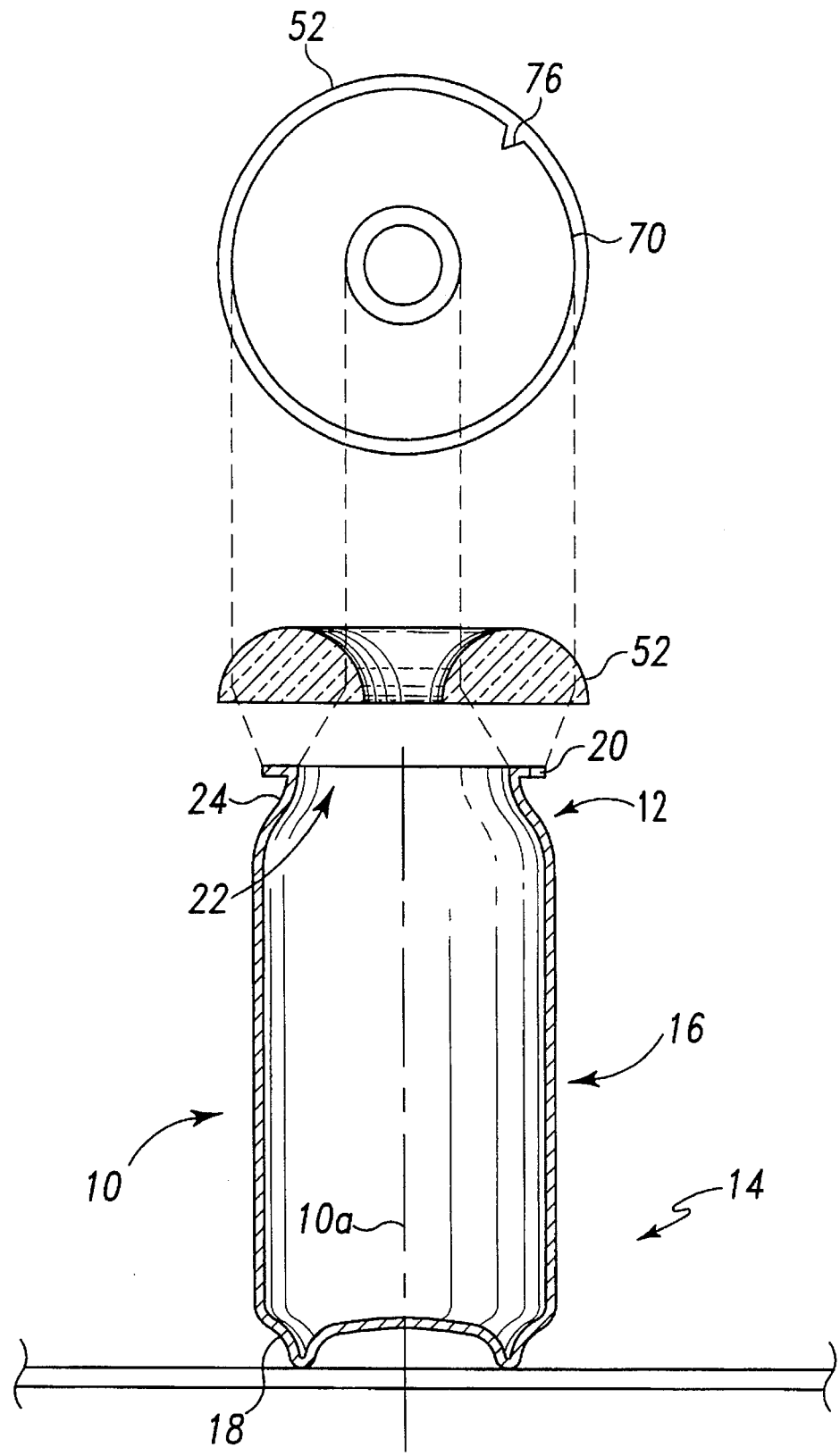
FIG. 4 shows an annular lens positioned above a container and a top view of an image of the flange expanded by the annular lens.
Figure 5A:
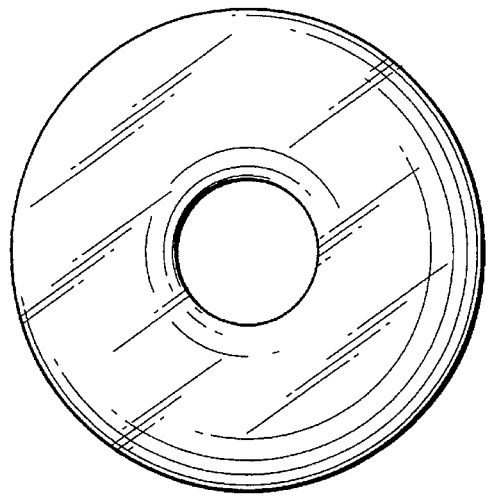
FIG. 5a–5e depict several alternative lens configurations.
Figure 5B:
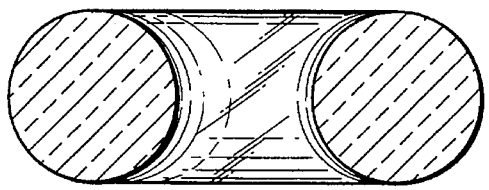
Figure 5C:
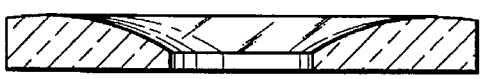
Figure 5D:
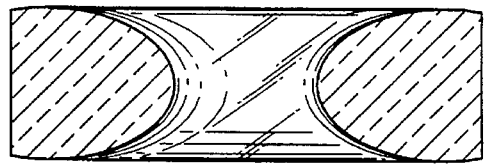
Figure 5E:

The operation of the system 30 used with this invention will now be described in more detail with specific reference to FIGS. 1, 2 and 4.

Referring now particularly to FIG. 2, with a container 10 in position at the inspection station 26, annular diode array 60 is operative to illuminate the flange 20 with diffused light rays 28a. Light rays 28a reflected from the flange 20 are then intercepted by annular lens 52 and redirected toward camera 54 as a flange image 70 (FIG. 4), corresponding to flange 20.

In the event a defect 72 exists on the flange 20 (FIG. 1), a corresponding defect image 76 (FIG. 4) appears in image 70 via annular lens 52. An enlarged defect image 76 is formed from light rays that are reflected irregularly from the defect 72 resulting in a light contrast in image 70 which can be detected optically by the camera 54 and analyzed by vision computer 64.

According to the present invention, an annular lens 52 is positioned between the flange 20 and the camera 54. The annular lens 52 expands the image 70 of the flange 20 so as to enlarge the image 76 of any defect in the flange 20, effectively improving the resolution of the camera 54. The flange image 70 is magnified by expanding the image radially inwardly, as best shown in FIG. 4. Importantly, the image 70 of the flange 20 is expanded preferentially at the expense of the image of the opening 22 thereby minimizing the image of the opening 22 and expanding the image 70 of the flange to substantially fill the viewing area of the camera 54. Accordingly, any edge defects 72, and any surface defects (not shown), are likewise expanded radially inwardly, and are stretched beyond the boundary of a single pixel. By stretching the defect 72 into two or more pixels, the annular lens 52 facilitates detection of a previously undetectable flaw, thereby permitting an inspection system to meet more stringent inspection requirements.

Of course, the annular lens 52 is not limited to a toroidal lens. Rather, based on the particular situation, the lens can have any one of several cross sections. For example, FIGS. 5a–5e show various possible cross sections which can be used depending on the size of the article to be inspected, the size of the camera lens and other factors. Thus, FIGS. 5b–5e are not meant to be an exhaustive selection of available cross sections available.

Although the invention has been described in detail with reference to a certain preferred embodiment, variations and modifications exist within the scope and spirit of the invention as described and defined in the following claims.

I claim:

1. An inspection apparatus for inspecting a circular container, the apparatus comprising:

means for producing an enlarged image of an upper surface of the container, and means for capturing and processing the enlarged image, wherein the producing means includes an annular lens with a annular convex portion which increases in thickness from its inner periphery positioned between the container and the capturing and processing means.

2. The apparatus of claim 1 wherein the annular lens is generally toroidal to produce an enlarged image of a peripheral edge of a flange surrounding an opening of the container.

3. The apparatus of claim 1 wherein the annular lens includes a first planar surface, a central axis orthogonal to the first planar surface, and a second surface, the second surface extending away from the first planar surface so as to provide a maximum lens thickness with said annular convex portion at a radial distance from its inner periphery.

4. The apparatus of claim 3 wherein the annular lens includes a peripheral edge and the second surface is curved to provide a maximum lens thickness at the radial distance from the central axis and a lesser thickness at the peripheral edge of the annular lens.

5. The apparatus of claim 1 wherein the annular lens expands the image of the selected portion of the container radially inwardly.

6. The apparatus of claim 1 wherein the means for capturing and processing includes means for analyzing a captured enlarged image for defects in the container.

7. The apparatus of claim 6 wherein the means for capturing and processing includes a video camera and the analyzing means includes a vision computer electronically coupled to the video camera, said vision computer identifying defects in the enlarged image with increased resolution.

8. The apparatus of claim 6 further comprising means for illuminating the container.

9. The apparatus of claim 8 wherein the means for illuminating includes an annular array of light emitting diodes arranged above an opening of the container for illuminating the container with diffused light rays.

10. An optical inspection apparatus for inspecting an article for defects, wherein the article includes an opening surrounded by a flange, the apparatus comprising:

a diffuser bowl positioned above the article, a light source disposed within the diffuser bowl for illuminating the flange of the article, image processing means positioned to receive light rays reflected by the flange, and an annular lens having an annular convex portion formed by increased thickness from its inner periphery disposed between the article and the image processing means for directing reflected light rays to produce a radially-expanded image of a peripheral edge of the flange for inspection.

11. The apparatus of claim 10 wherein the annular lens includes a central axis and the image processing means includes a camera movable along the central axis relative to the annular lens to expand the image of the peripheral edge of the flange.

12. The apparatus of claim 10 wherein the annular lens expands the image of the flange radially inwardly.

13. The apparatus of claim 10 wherein the annular lens is symmetric about the central axis and includes a first curved surface forming said annular convex portion.

14. The apparatus of claim 13 wherein the annular lens further includes a second curved surface, the first and second curved surfaces cooperating to provide a maximum lens thickness at a radial distance from the central axis.

15. The apparatus of claim 10 wherein the image of the peripheral edge of the flange includes an image of the flange and an image of at least a portion of the opening, and the annular lens expands the image of the flange radially inwardly while reducing the image of the at least a portion of the opening.

16. A method for inspecting a flange of a circular article for defects, the method comprising the steps of:

directing light onto the flange of the article from a light source, forming light rays reflected from the article flange into a expanded image of at least a portion of the article flange and any defects therein by positioning an annular lens, having an annular convex portion which increases in thickness as it expands from its inner periphery, to redirect said reflected light rays into said expanded image, and providing means for capturing and processing the expanded image to inspect the article for defects.

17. The method of claim 16 wherein the annular lens includes a central axis and the lens is configured to include a maximum lens thickness at a first radial distance from the central axis and a minimum lens thickness at a second radial distance from the central axis.

18. The method of claim 17 wherein the article includes a flange surrounding an opening and the lens is positioned to expand the image of the flange radially inwardly while simultaneously reducing an image of the opening.

19. The method of claim 16 wherein the means for capturing and processing includes a video camera having a lens and a vision computer, the video camera lens being movable along the central axis relative to the annular lens to expand the captured image.

20. The method of claim 16 wherein said means for capturing and processing the expanded image digitalizes the expanded image into pixel information, analyzes the pixel information and identifies any unacceptable defect from their expanded images.

21. An optical inspection apparatus for inspecting a plurality of flange containers for defects in a container flange, the apparatus comprising:

means for carrying a flanged container to an inspection station to be inspected, a light source for illuminating the container flange, an image sensor positioned to receive light rays reflected from the container flange, and a lens, having an annular convex portion which increases in thickness as it expands from its central axis, disposed between the container and an image sensor for enlarging at least a portion of the flange for inspection by expanding the image of the flange radially inwardly.

22. The apparatus of claim 21 wherein the lens is an annularly-shaped lens.

23. The apparatus of claim 21 further comprising a vision computer comprising means for converting the expanded image of the flange into digital information, and means for analyzing the digital information to identify digital information corresponding to an unacceptable defect in the flange, and means for providing an output in the event an unacceptable defect is identified.

24. An inspection apparatus for inspecting a circular object, the apparatus comprising:

a lens having an annular convex portion which increases in thickness as it expands radially outwardly of the lens' center for radially expanding an image of at least an annular portion of the object; and means for capturing and processing the image.

25. The apparatus of claim 24 further comprising means for illuminating the object.

26. The apparatus of claim 24 wherein the capturing and processing means includes a camera and a vision computer.

27. An inspection apparatus for inspecting an annular object, the apparatus comprising:

a camera having a field of view; and a lens having an annular convex portion for magnifying an image of the annular object radially inwardly while retaining the image in the camera's field of view.

* * * * *